United States Patent [19]

Bang et al.

[11] Patent Number: 5,416,081
[45] Date of Patent: May 16, 1995

[54] CEPHALOSPORIN COMPOUNDS

[75] Inventors: Chan S. Bang; Yong Z. Kim; Jae H. Yeo; Jong C. Lim; Hun S. Oh; Young M. Woo; Duk H. Yang; Sam S. Kim; Hyeon J. Yim, all of Daejeon, Rep. of Korea

[73] Assignee: Lucky Limited, Seoul, Rep. of Korea

[21] Appl. No.: 171,535

[22] Filed: Dec. 22, 1993

[30] Foreign Application Priority Data

Dec. 26, 1992 [KR] Rep. of Korea ............... 92-25647

[51] Int. Cl.$^6$ ............... C07D 501/36; A61K 31/545
[52] U.S. Cl. ............................ 514/206; 540/227
[58] Field of Search ............... 540/222, 227; 514/206

[56] References Cited

U.S. PATENT DOCUMENTS 5,202,315 4/1993 Kim et al. .................. 540/227

FOREIGN PATENT DOCUMENTS 248645 3/1987 European Pat. Off. .
397511 11/1990 European Pat. Off. .
WO92/03445 1/1991 WIPO .

Primary Examiner—Nicholas Rizzo
Attorney, Agent, or Firm—William F. Pinsak

[57] ABSTRACT

The present invention relates to novel cephalosporin compounds, pharmaceutically acceptable non-toxic salts, physiologically hydrolyzable esters, hydrates and solvates and isomers thereof which possess potent and broad antibacterial activities. The compounds of the present invention have a (4-amino-1-substituted-alkapyrimidinium-4-yl)thiomethyl group in 3-position of the cephem nucleus and is specifically represented by the following formula(I):

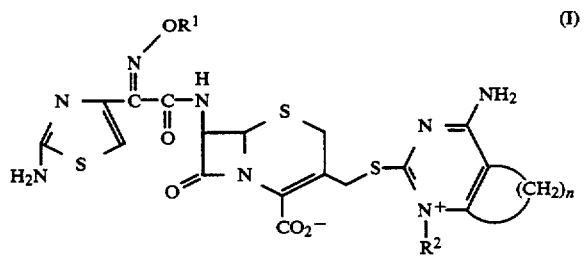

wherein:

$R^1$ is a hydrogen atom or a $C_{1-4}$ alkyl, $C_{2-4}$ alkenyl, $C_{2-4}$ alkynyl or —$C(R^A)(R^B)$COOH group wherein $R^A$ and $R^B$ are independently a hydrogen atom or a $C_{1-4}$ alkyl group, or form a $C_{3-7}$ cycloalkyl group together with the carbon atom to which they are attached;

$R^2$ is an unsubstituted or substituted amino, $C_{1-4}$ alkyl or $C_{3-7}$ cycloalkyl group; and n is an integer ranging from 2 to 7.

3 Claims, No Drawings

CEPHALOSPORIN COMPOUNDS

FIELD OF THE INVENTION

The present invention relates to novel cephalosporin compounds, and pharmaceutically acceptable non-toxic salts, physiologically hydrolyzable esters, hydrates and solvates, and isomers thereof, which possess potent and broad spectrum of antibacterial activities. The invention also relates to pharmaceutical compositions containing same as active ingredients.

DESCRIPTION OF THE PRIOR ART

Antibiotics of cephalosporin series are widely used in therapy for the treatment of diseases which are caused by general pathogenic bacteria in human beings and animals. It has been known that such antibiotics are useful for the treatment of diseases caused by bacteria exhibiting resistance to other antibiotics, e.g., penicillin-resistant bacteria; and also for the treatment of penicillin-sensitive patients.

In most circumstances, it is desirable to employ antibiotics possessed with a wide range of antibacterial activities, e.g., against both Gram-positive and Gram-negative bacteria. It is well known that the activity of a cephalosporin compound depends upon the substituent on the 3- or 7-position of the cephem ring. In this regard, there are many studies made in developing a variety of cephalosporin antibiotics with such broad spectrum of antibiotic activities by introducing a 7-β acylamido group and various substituents on the 3-position of the cephem ring.

For example, Japanese Laid-open Patent Publication No. 54-9296 discloses a cephalosporin derivative having a substituent X, on the 3-position of the cephem ring, of the following formula(A):

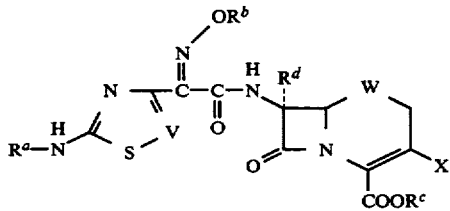

(A)

wherein X Represents a hydrogen or halogen atom, or an optionally substituted alkyloxy or alkenyloxy or —CH$_2$Y group where Y represents a hydrogen, halogen or moiety of a nucleophilic compound including —SR where R represents an optionally substituted 5- to 8- membered heterocyclic ring.

French Patent No. 2,426,694 provides a 7-[(2-aminothiaxol-4-yl)-2-oxyiminoacetamido]cephem derivative having certain substituents, in the 7β- and 3-positions, of the formula(B):

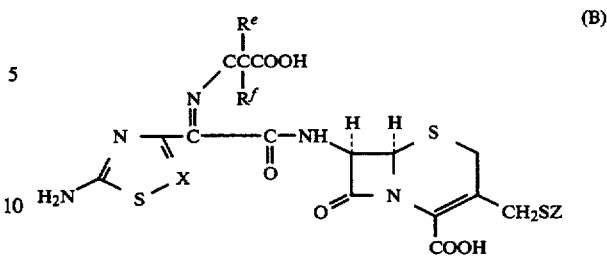

(B)

wherein R$^e$ and R$^f$ together form a C$_{3\text{-}7}$ cycloalkylidene group with the carbon atom to which they are linked; and Z represents a 5- or 6-membered heterocyclic ring, linked to a carbon atom, which contains one or more nitrogen atom, and may contain one or more sulfur atom and/or may be substituted with a C$_{1\text{-}4}$ alkyl group. European Patent Application No. 87304896.1 discloses a cephalosporin compound of the formula(C):

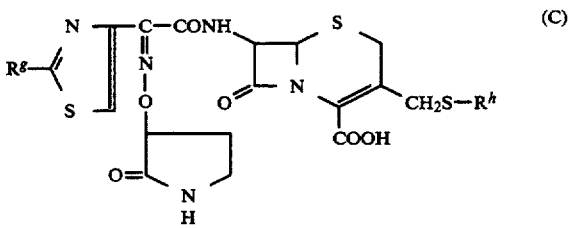

(C)

wherein R$^h$ represents

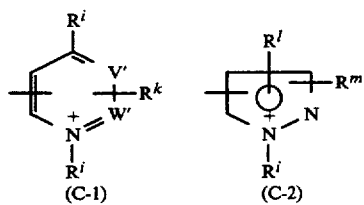

(C-1)  (C-2)

wherein R$^i$ represents a lower alkenyl, optionally substituted 5- or 6- membered nitrogen-containing heterocyclic group, acylamino or optionally substituted lower alkyl group; R$^j$ and R$^k$, which may be the same or different, are each independently a hydrogen, lower alkyl, amino, acylamino, carboxyl, carbamoyl, thiocarbamoyl or lower alkoxycarbonyl group; R$^l$ and R$^m$ are each independently a lower alkyl group; and V' and W', which may be the same or different, are each independently —CH= or —N= group.

Further, cephalosporin compounds having various 4,6-diaminopyrimidinium moiety on the 3-position, with improved properties with respect to certain microorganisms, especially against Gram-negative bacteria, of the following formula(D) are disclosed in Korean Patent Nos. 47728, 47754, 47755 and 47756:

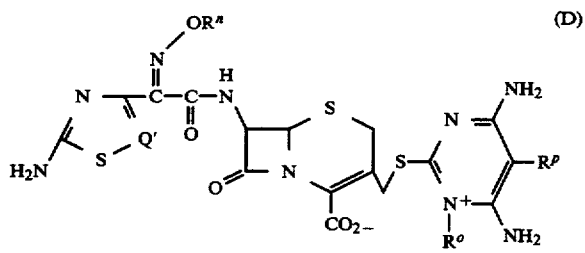
(D)

wherein $R^n$ is a $C_{1-4}$ alkyl, $C_{3-4}$ alkenyl, $C_{3-4}$ alkynyl or $C(R^a)(R^b)COOH$ (wherein $R^a$ and $R^b$ are independently a hydrogen atom or a $C_{1-4}$ alkyl group, or form a $C_{3-7}$ cycloalkyl group together with the carbon atom to which they are attached); $R^o$ is a $C_{1-4}$ alkyl, $C_{3-4}$ alkenyl, $C_{3-4}$ alkynyl, or optionally substituted amino or phenyl group; $R^p$ represents a hydrogen or $C_{1-4}$ alkyl group; and $Q'$ is CH or N.

Korean Patent Application No. 91-6494, which was filed on Apr. 23, 1991 and is now pending, is directed to a cephalosporin compound of formula (E):

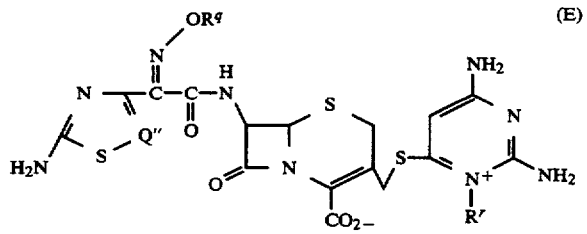
(E)

wherein $R^q$ is a hydrogen atom or a $C_{1-4}$ alkyl, $C_{2-4}$ alkenyl, $C_{2-4}$ alkynyl group or —$C(R^a)(R^b)COOH$ group(wherein $R^a$ and $R^b$ have the same meanings as defined in the above formula(D)); $R^r$ is a $C_{1-4}$ alkyl, carboxymethyl, hydroxyethyl or amino group; and $Q''$ is N or CH.

Further, EPA 150,507 discloses a cephem compound of formula(F)

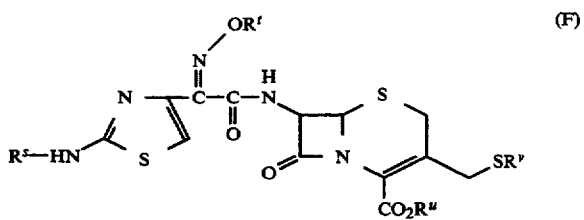
(F)

wherein $R^s$ is a hydrogen atom or an amino protecting group; $R^t$ is a hydrogen atom or a methyl, hydroxy or acyl group; $R^u$ is a hydrogen atom or a carboxyl protecting group; and $R^v$ is a heterocyclic group, particularly a triazolopyrimidyl or thiazolopyrimidyl group.

However, none of the above-mentioned prior art literatures has disclosed or taught the possibility of employing a (4-amino-1-substituted-cycloalkapyrimidinium-4-yl) thiomethyl group as a substitutent in the 3-position of the cephem nucleus.

SUMMARY OF THE INVENTION

The present inventors have studied for a long time in search for a cephalosporin compound which has a broad spectrum of antibiotic activities. As a result, the present inventors have discovered that cephalosporin compounds with a (4-amino-1-substituted-cycloalkapyrimidinium-4-yl)thiomethyl group in the 3-position and a certain group in the 7-β-position of the cephem nucleus exhibit strong antibacterial activities in a broad spectrum.

Accordingly, the primary object of the present invention is to provide said novel cephalosporin compounds.

It is another object of the present invention to provide pharmaceutical compositions containing same.

In accordance with one aspect of the present invention, there is provided with novel cephalosporin compounds of formula(I):

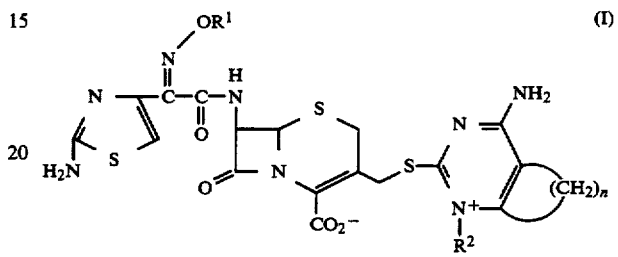
(I)

wherein:

$R^1$ is a hydrogen atom or a $C_{1-4}$ alkyl, $C_{2-4}$ alkenyl, $C_{2-4}$ alkynyl or —$C(R^A)(R^B)COOH$ group wherein $R^A$ and $R^B$ are independently a hydrogen atom or a $C_{1-4}$ alkyl group, or form a $C_{3-7}$ cycloalkyl group together with the carbon atom to which they are attached;

$R^2$ is an unsubstituted or substituted amino, $C_{1-4}$ alkyl or $C_{3-7}$ cycloalkyl group; and n is an integer ranging from 2 to 7.

In accordance with another aspect of the present invention, there is provided with pharmaceutically acceptable non-toxic salts, physiologically hydrolyzable esters, hydrates and solvates, and isomers of the compounds of formula(I).

In accordance with a further aspect of the present invention, there is provided with pharmaceutical compositions comprising one or more of the cephalosporin compounds represented by formula(I) and their aforementioned derivatives as active ingredients and their pharmaceutically acceptable carriers.

DETAILED DESCRIPTION OF THE INVENTION

The novel cephalosporin compounds of formula(I) include both syn isomers and mixtures of Syn and anti isomers which mixtures contain at least 90% of the syn isomer. With respect to the radical, —O—$C(R^A)(R^B)$—COOH, the compounds of formula(I) also include the diastereomeric isomers and mixtures thereof when $R^A$ and $R^B$ are different from each other.

In addition, the compounds of formula(I) in accordance with the present invention may exist in tautomeric forms and such tautomers are also included within the scope of the invention. Namely, the aminothiazolyl group undergoes tautomerism to form an iminothiazolinyl group, its tautomer, as follows:

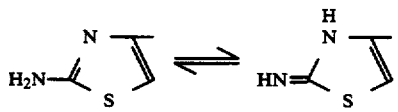

Among the compounds of the present invention, preferred compounds are those wherein: $R^1$ is a methyl, ethyl or —$C(R^A)(R^B)COOH$ group wherein $R^A$ and $R^B$ are independently a hydrogen atom or a methyl or ethyl group, or form an unsubstituted $C_{5-6}$ cycloalkyl group together with the carbon atom to which they are attached, or allyl or propagyl group; $R^2$ is a methyl or amino group; and n is 3 or 4.

Exemplary compounds of formula(I) are listed in Table 1.

TABLE 1

Exemplary Compounds of formula(I)

(I)

| Compound | $R^1$ | $R^2$ | n |
|---|---|---|---|
| I-1 | —$(CH_3)_2CO_2H$ | —$NH_2$ | 3 |
| I-2 | —$(CH_3)_2CO_2H$ | —$CH_3$ | 3 |
| I-3 | —$(CH_3)_2CO_2H$ | —$NH_2$ | 4 |
| I-4 | —$(CH_3)_2CO_2H$ | —$CH_3$ | 4 |
| I-5(S) | —*CH$(CH_3)_2CO_2H$ | —$NH_2$ | 3 |
| I-5(R) | —*CH$(CH_3)_2CO_2H$ | —$NH_2$ | 3 |
| I-6(S) | —*CH$(CH_3)_2CO_2H$ | —$CH_3$ | 3 |
| I-7(S) | —*CH$(CH_3)_2CO_2H$ | —$NH_2$ | 4 |
| I-8 | —$CH_2CO_2H$ | —$NH_2$ | 3 |
| I-9 | —$CH_2CO_2H$ | —$CH_3$ | 3 |
| I-10 | —$CH_3$ | —$NH_2$ | 3 |
| I-11 | cyclopentyl-CO$_2$H | —$NH_2$ | 3 |
| I-12 | cyclopentyl-CO$_2$H | —$CH_3$ | 3 |
| I-13(S) | —*CH$(C_2H_5)CO_2H$ | —$NH_2$ | 3 |
| I-13(R) | —*CH$(C_2H_5)CO_2H$ | —$NH_2$ | 3 |
| I-14(R) | —*CH$(C_2H_5)CO_2H$ | —$CH_3$ | 3 |
| I-15(S) | isobutyl-CO$_2$H | —$NH_2$ | 3 |
| I-15(R) | isobutyl-CO$_2$H | —$NH_2$ | 3 |
| I-16(R) | isobutyl-CO$_2$H | —$CH_3$ | 3 |
| I-17 | —$CH_2CH_3$ | —$NH_2$ | 3 |
| I-18 | —$CH_2CH_3$ | —$NH_2$ | 4 |
| I-19 | —$CH_2CH_3$ | —$CH_3$ | 3 |

Furthermore, the present invention encompasses, within its scope, those pharmaceutically acceptable non-toxic salts, physiologically hydrolyzable esters, solyates and hydrates of the compounds of formula(i). Suitable pharmaceutically acceptable salts of the cephalosporin compounds(I) are conventional non-toxic salts and may include: inorganic acid salts(e.g., hydrochloride, hydrobromide, sulfate, phosphate and the like); organic carboxylic and sulfonic acid salts(e.g., formate, trifluoroacetate, citrate, acetate, maleate, tartrate, oxalate, succinate, benzoate, fumarate, mondelate, ascorbate, malate, methanesulfonate, paratoluenesulfonate and the like); and also, depending on $R^1$, inorganic and organic base salts such as salts with alkali metal hydroxides(e.g., sodium hydroxide, potassium hydroxide and the like), alkaline earth metal hydroxides (e.g., calcium hydroxide and the like), sodium bicarbonate, potassium bicarbonate, sodium carbonate, potassium carbonate and calcium carbonate, and amino acid salts.

Above pharmaceutically acceptable non-toxic salts may be prepared in accordance with known methods, e.g., by reacting the compounds of the formula(I) with one to four equivalents of corresponding acids or bases to form the salts mentioned above in the presence of a solvent which may be water, or a mixture of water and water-miscible solvent(e.g., methanol, ethanol, acetonitrile, acetone and the like).

The physiologically hydrolyzable esters of the compounds(I) may include, for example, indanyl, phthalidyl, methoxymethyl, pivaloyloxymethyl, glycyloxymethyl, phenylglycyloxymethyl and 5-methyl-2-oxo-1,3-dioxolan-4-yl esters, and other physiologically hydrolyzable esters which have been widely used in the penicillin and cephalosporin antibiotics art.

These esters can be prepared in accordance with known methods, e.g., by reacting the compounds of formula(I) with a corresponding alkyl halide(e.g., methoxymethyl chloride) in the presence of a base(e.g., triethylamine, pyridine or sodium bicarbonate).

Exemplary solvates of the cephalosporin compounds of formula(I) may include those solvates with water-miscible solvents, e.g., methanol, ethanol, acetone and acetonitrile, preferably, ethanol.

The present invention also includes within its scope pharmaceutical compositions comprising one or more of the compounds(I) and their above-mentioned derivatives as active ingredients, in association with pharmaceutically acceptable carriers, excipients or other additives, if necessary.

The pharmaceutical compositions of the invention may be formulated for administration in unit dose or multi-dose containers. The compositions may take various forms such as solution, suspension or emulsion in an oily or aqueous vehicle, which can contain conventional additives such as a dispersant, suspending agent, stabilizer and the like. Alternatively, the active ingredient may be formulated into a dried powder that can be normally dissolved in an aqueous solution of sterile pyrogen-free water before use. The compositions may be also formulated into suppositories containing conventional suppository bases such as cocoa butter or other glycerides.

The pharmaceutical compositions in a unit dose form may preferably comprise about 50 to 1,500 mg of the active ingredient, depending on the age and body weight of the patient, the nature and severity of the illness, and so on. In general, it has been shown advantageous to administer the active compounds in an amount ranging from 500 to 5,000 mg per day in order to achieve the desired results, depending on the routes and frequency of administration. In case of intramuscular or intravenous administration for adult human treatment, the dosage of about 150 to 3,000 mg per day is thought to be sufficient, although it may vary in case of treatment for specific infections caused by certain strains.

The compounds of the present invention and non-toxic salts thereof(preferably, alkali or alkaline earth metal salts, organic and inorganic salts and amino acid salts), as described above, exhibit potent and broad antibacterial activities against Gram-positive bacteria and a variety of Gram-negative bacteria as well particularly against Pseudomonas. Also, these compounds have high stability to β-lactamases produced by a number of Gram-negative bacteria.

A compound of formula(I) may be prepared by reacting a compound of formula(II) with a compound of formula(III) in the presence of a solvent, and, if necessary, removing the amino or carboxyl protecting group or reducing an S-oxide[S→(O)$_n$]:

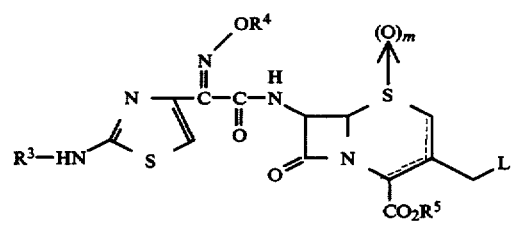
(II)

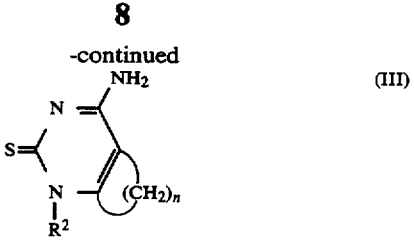
(III)

wherein:
$R^2$ and n have the same meanings as defined above;
$R^3$ is a hydrogen or an amino protecting group;
$R^4$ is a hydrogen atom, or a $C_{1-4}$ alkyl, $C_{2-4}$ alkenyl, $C_{2-4}$ alkynyl or —C($R^A$)($R^B$)—COOR$^C$ group wherein $R^A$ and $R^B$ are independently a hydrogen atom or a $C_{1-4}$ alkyl group, or together with the carbon atom to which they are attached, form a $C_{3-7}$ cycloalkyl group; and $R^C$ is a hydrogen or a carboxyl protecting group;
$R^5$ is a hydrogen or a carboxyl protecting group;
L is a leaving group; and
m is 0 or 1.

The amino protecting group of $R^3$ above may be those groups which can be readily removed under a conventional mild condition to form a free amino group and may include: acyl, substituted and unsubstituted aryl(lower)alkyl(e.g., benzyl, diphenylmethyl and triphenylmethyl), (lower)alkoxyaryl (e.g., 4-methoxybenzyl), halo(lower)alkyl(e.g., trichloro-methyl and trichloroethyl), tetrahydropyranyl, substituted phenylthio, substituted alkylidene, substituted aralkylidene and substituted cycloalkylidene. The acyl group as an amino protecting group may include, for example, $C_{1-6}$ alkanoyl(e.g., formyl and acetyl), $C_{2-6}$ alkoxycarbonyl-(e.g., methoxycarbonyl and ethoxycarbonyl), (lower)alkanesulfonyl (e.g., methanesulfonyl and ethanesulfonyl), and aryl(lower)alkoxycarbonyl (e.g., benzyloxycarbonyl), where the acyl group can be substituted with 1 to 3 substituents such as a halogen atom, a hydroxy, cyano and nitro group. In addition, the amino protecting group may include the reaction products obtained from reacting the amino group with a silane, boron or phosphorous compound.

The carboxyl protecting group of $R^C$ or $R^5$ may be any of those which can be readily removed under a conventional mild condition to form a free carboxyl group and may include, for example, (lower)alkylesters-(e.g., methyl ester and tert-butyl ester), (lower)alkenylesters(e.g., vinylester and allylester), (lower)alkoxy(lower)alkylesters(e.g., methoxymethylester), (lower)alkylthio(lower)alkylesters(e.g., methylthiomethylester), halo(lower)alkylesters(e.g., 2,2,2-trichloroethylester), substituted and unsubstituted aralkyl esters(e.g., benzylester and p-nitrobenzyl ester), (lower) aralkoxy esters(e.g., p-methoxybenzylester) and silyl esters. The amino or carboxyl protecting group can be properly selected after considering the chemical property of the desired compound(I).

The leaving group L in formula(II) may include, for example, a halogen atom such as chlorine and fluorine, a (lower) alkanoyloxy group such as acetoxy, a (lower)alkanesulfonyloxy group such as methanesulfonyloxy, an arenesulfonyloxy group such as p-toluenesulfonyloxy, an alkoxycarbonyloxy group and the like.

The term "lower" as used hereinabove and elsewhere in this specification, for example, in reference to "lower alkyl," encompasses those compounds having 1 to 6 carbon atoms, preferably, 1 to 4 carbon atoms.

The starting materials of the compounds(II) are known intermediates conventionally employed for the preparation of cephalosporin compounds. The dotted line of formula(II) represents a single or double bond; and, therefore, the compounds of formula(II) may be of formula(II-a) or formula (II-b), or mixtures thereof:

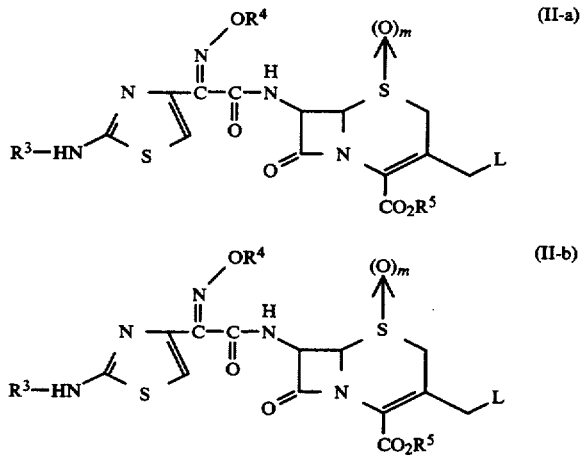

wherein m, $R^3$, $R^4$, $R^5$ and L have the same meanings as defined before.

The compounds of formula(II) may be prepared by activating the compounds of formula(IV) or salts thereof with an acylating agent and then reacting with the compounds of formula(V) in accordance with the following scheme(A).

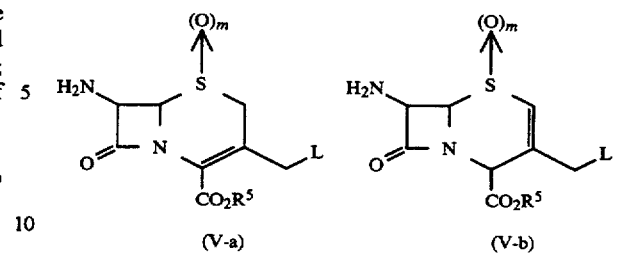

wherein:
m, $R^5$ and L have the same meanings as defined previously

The acylated derivative of the compound of formula(IV) may be an acid chloride, anhydrous acid, mixed anhydrous acid (preferably, anhydrous acid formed with methyl chloroformate, mesitylenesulfonyl chloride, p-toluenesulfonyl chloride or chlorophosphate) or activated ester (preferably, an ester formed by the reaction with N-hydroxy benzotriazole in the presence of a condensing agent, e.g., dicyclohexyl carbodiimide). The acylation may be conducted by using a free acid of the compound IV) in the presence of a condensing agent, e.g., dicyclohexyl carbodiimide or carbonyl diimidazole. Further, the acylation may be conventionally conducted in the presence of an organic base, e.g., a tertiary amine(preferably, triethyl amine), diethylaniline and pyridine, or an inorganic base, e.g., sodium bicarbonate and sodium carbonate, and a solvent, e.g., a halogenated hydrocarbon (e.g., methylene chloride and chloroform), tetrahydrofuran, acetonitrile, dimethyl Scheme A

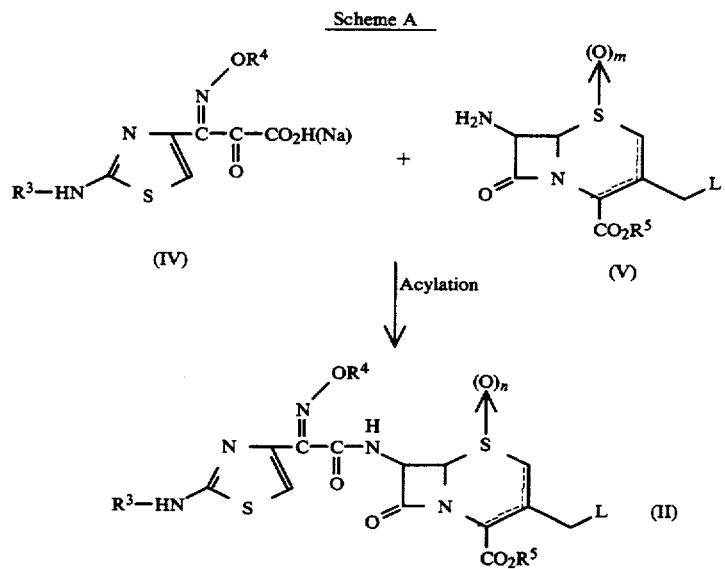

wherein:
$R^3$, $R^4$, $R^5$ and L have the same meanings as defined previously.

The dotted line of formula(V) represents a single or double bond; and therefore, the compounds of formula(V) may be of formula(V-a) or of formula(V-b), or mixtures thereof:

formamide and dimethyl acetamide and a mixture thereof and an aqueous mixture thereof.

The acylation may be conducted at a temperature ranging from $-50°$ C. to $50°$ C., preferably from $-30°$ C. to $20°$ C., and the acylating agent may be used in a stoichiometric amount, or an excess(1.05 to 1.2 equivalents) thereof, based on the compound of formula(V).

In order to prepare the compound of formula(I), amino or carboxyl protecting groups of formula(II) can be readily removed by a conventional deprotecting method which is well known in the field of cephalosporin antibiotics. For example, acid- or base-hydrolysis or reduction is generally applicable. For example, when the compound of formula(II) contains an amido group as a protecting group, the compound may be subjected to an aminohalogenation, aminoetherification or hydrolysis procedure. The acid-hydrolysis is suitable for removing a tri(di)phenylmethyl or alkoxycarbonyl group; and may be conducted by employing an organic acid, e.g., formic acid, trifluoroacetic acid and p-toluenesulfonic acid, or an inorganic acid, e.g., hydrochloric acid.

The compounds of formula(III) used in the present invention are novel materials. The process for the preparation of the compound(III) is specifically disclosed in the following Preparation Examples.

The reaction for introducing the compound(III) into the 3-position of the compound(II) to prepare the compound(I) is carried out in the presence of a solvent such as a polar solvent, e.g., N,N-dimethylformamide, dimethylsulfoxide, N,N-dimethylacetamide and the like, wherein the temperature may range from 10° to 80° C., preferably from 20° to 40° C.; and the compounds of formula(III) are used in an amount ranging from 0.5 to 2, preferably from 0.9 to 1.1 molar equivalent, based on the compounds of formula(II).

Reduction of S-oxide can be conventionally carried out, for example, by adding potassium iodide and acetyl chloride to the reactants, followed by quenching the reaction mixture with sodium m-bisulfite.

The separation and purification of the compounds(I) can be carried out by using a conventional method such as recrystallization, column chromatography over silica gel or ion-exchange chromatography.

The following Preparation Examples and Examples illustrate how the starting materials of formulae(II) and (III) and of the compounds of formula(I) can be prepared.

Preparation Example 1: Synthesis of 1,4-diamino-1,5,6,7-tetrahydrocyclopentapyrimidine-2-thione Step 1) Synthesis of 6,7-dihydro-5H-cyclopentapyrimidine-2,4-diol To a solution of 100 g of ethyl 2-oxocyclopentane carboxylate dissolved in 100 ml of ethyl alcohol was added 120 g of urea. The reaction solution was heated to reflux at 160° C. for 5 hours and cooled to room temperature to produce precipitates, which were washed with 200 ml of acetone and dried. The solids thus obtained were suspended into 200 ml of a distilled water and the resulting suspension was slowly stirred at room temperature for 10 hours and filtered to obtain solids, which were washed with 50 ml of a distilled water and 100 ml of acetone and dried to obtain 40 g of the title compound as a white powder.

NMR($\delta$, DMSO-$d_6$): 1.92(m, 2H), 2.42(t, 2H), 2.61(t, 2H), 10.70(S, 1H), 11.02(s, 1H)

Step 2) Synthesis of 2,4-dichloro-6,7-dihydro-5H-cyclopentapyrimidine 20 g of the compound obtained in Step 1 was charged into 100 ml of phosphorous oxychloride. The reaction mixture was heated under reflux for 2 hours and distilled under reduced pressure to remove the solvent. The residue was poured into 500 ml of an iced water and neutralized with 28% ammonium hydroxide. The resultant solution was extracted with 200 ml of ethyl acetate, and the organic layer was dried over anhydrous magnesium sulfate and distilled under reduced pressure to obtain 19 g of the title compound as a white solid.

NMR($\delta$, DMSO-$d_6$): 2.06(m, 2H), 2.89(t, 2H), 3.01(t, 2H)

Step 3) Synthesis of 2-chloro-6,7-dihydro-5H-cyclopentapyrimidine-4-yl amine 10 g of the compound obtained in Step 2 was dissolved in 300 ml of ethyl alcohol. To the resulting solution was added 150 ml of 28% ammonium hydroxide and the solution was stirred at 40° C. for 14 hours. The reaction solution was distilled under reduced pressure to remove the ethanol solvent and filtered to collect solids, which were washed with 20 ml of distilled water and 20 ml of hexane to obtain 8 g of title compound as a white powder.

NMR($\delta$, DMSO-$d_6$): 1.93(m, 2H), 2.57(t, 2H), 2.68(t, 2H), 7.10(s, 2H).

Step 4) Synthesis of 1,4-diamino-1,5,6,7-tetrahydrocyclopentapyrimidine-2-thione 5 g of the compound obtained in Step 3 was dissolved in 100 ml of dichloromethane and the resulting solution was cooled to a temperature ranging from $-50°$ to $-60°$ C. To the cold solution was slowly added over 10 minutes a solution of 10 g of mesitylenesulfonyl hydroxylamine dissolved in 20 ml of dichloromethane. The resulting solution was warmed to room temperature, stirred for additional 10 minutes and filtered to collect solids, which were washed with 20 ml of diethyl ether and dried to obtain white solids. The solids were dissolved in 100 ml of methanol, and 2.5 g of sodium hydrogen sulfide was added thereto. The resulting solution was stirred at room temperature for 30 minutes and filtered to provide solids, which were washed with 10 ml of distilled water and 10 ml of acetone and dried to obtain 3 g of the title compound as a white powder.

m.p.: >215° C.(decomposition)

NMR($\delta$, DMSO-$d_6$): 2.01(m, 2H), 2.69(t, 2H), 2.93(t, 2H), 6.53(s, 2H), 7.91(bs, 2H)

Preparation Example 2: Synthesis of 4-amino-1-methyl-1,5,6,7-tetrahydro-cyclopentapyrimidine-2-thione 5 g of 2-chloro-6,7-dihydro-5H-cyclopentapyrimidine-4-yl amine obtained in Step 3 of Preparation Example 1 was dissolved in 100 ml of tetrahydrofuran and thereto was added 10 g of methyl iodide. The resultant mixture was heated to reflux for 8 hours, cooled to room temperature and filtered to obtain precipitates, which were washed with 20 ml of diethyl ether and dried to obtain white solids. The solids were dissolved in 100 ml of methanol, and 2.5 g of sodium hydrogen sulfide was added thereto. The resulting solution was stirred at room temperature for 30 minutes and filtered to provide solids, which were washed with 10 ml of distilled water and 10 ml of acetone and dried to obtain 3.2 g of the title compound as a white powder.

m.p.: >220° C.(dec.)

NMR($\delta$, DMSO-$d_6$): 1.92(m, 2H), 2.52(t, 3H), 2.90(t, 3H), 7.20(s, 2H)

Preparation Example 3: Synthesis of 1,4-diamino-5,6,7,8-tetrahydro-1H-quinazoline-2-thione Step 1) Synthesis of 5,6,7,8-tetrahydro-quinazoline-2,4-diol To a solution of 100 g of ethyl 2-cyclohexanone carboxylate dissolved in 100 ml of ethyl alcohol was added 120 g of urea. The reaction solution was heated to reflux at 160° C. for 4 hours and cooled to room temperature to produce precipitates, which were washed with 200 ml of acetone and dried. The solids thus obtained were suspended into 200 ml of distilled water and the resulting suspension was slowly stirred at room temperature for 10 hours and filtered to obtain solids, which were washed with 100 ml of distilled water and 100 ml of acetone and dried to obtain 47 g of the title compound as a white powder.

NMR(δ, DMSO-d6): 1.68(m, 4H), 2.36(t, 2H), 2.62(t, 2H), 10.51(s, 1H), 10.78(s, 1H)

Step 2) Synthesis of 2,4-dichloro-5,6,7,8-tetrahydroquinazoline 20 g of the compound obtained in Step 1 was charged into 100 ml of phosphorous oxychloride. The reaction mixture was heated under reflux for 2 hours and distilled under reduced pressure to remove the solvent. The residue was poured into 500 ml of an iced water and neutralized with 28% ammonium hydroxide. The resultant solution was extracted with 300 ml of ethyl acetate and the organic layer was dried over anhydrous magnesium sulfate and distilled under reduced pressure to obtain 18 g of the title compound as a white solid.

NMR(δ, DMSO-d6): 1.72(m, 4H), 2.26(t, 2H), 2.49(t, 2H)

Step 3) Synthesis of 2-chloro-5,6,7,8-tetrahydroquinazoline-4-yl amine 10 g of the compound obtained in Step 2 was dissolved in 300 ml of ethyl alcohol. To the resulting solution was added 150 ml of 28% ammonium hydroxide and the solution was stirred at 40° C. for 10 hours. The reaction solution was distilled under reduced pressure to remove the ethanol solvent and filtered to provide solids, which were washed with 20 ml of distilled water and 20 ml of hexane to obtain 8.2 g of title compound as a white powder.

NMR(δ, CDCl3): 1.88(m, 4H), 2.34(t, 2H), 2.71(t, 2H), 5.46(s, 2H)

Step 4) Synthesis of 1,4-diamino-5,6,7,8-tetrahydro-1H-quinazoline-2-thione 5 g of the compound obtained in Step 3 was dissolved in 100 ml of dichloromethane and the resulting solution was cooled to a temperature ranging from −50° to −60° C. To the cold solution was slowly added a solution of 10 g of mesitylene sulfonyl hydroxylamine dissolved in 20 ml of dichloromethane. The resulting solution was warmed to room temperature, stirred for additional 10 minutes and filtered to provide solids, which were washed with 20 ml of diethyl ether and dried to obtain white solids. The solids were dissolved in 100 ml of methanol, and 2.5 g of sodium hydrogen sulfide was added thereto. The resulting solution was stirred at room temperature for 30 minutes and filtered to provide solids, which were washed with 10 ml of distilled water and 10 ml of acetone and dried to obtain 3.2 g of the title compound as a white powder.

m.p.: >225° C.(dec.)

NMR(δ, DMSO-d6): 1.63(m, 4H), 2.19(t, 2H), 2.38(t, 2H), 6.45(s, 2H), 6.9–7.2(bs, 2H)

Preparation Example 4: Synthesis of 4-amino-1-methyl-5,6,7,8-tetrahydro-1H-quinazoline-2-thione 5 g of 2-chloro-5,6,7,8-tetrahydro-quinazoline-4-yl amine obtained in Step 3 of Preparation Example 3 was dissolved in 100 ml of tetrahydrofuran and thereto was added 10 g of methyl iodide. The resultant mixture was heated to reflux for 8 hours, cooled to room temperature and filtered to obtain precipitates, which were washed with 20 ml of diethyl ether and dried to obtain white solids. The solids were dissolved in 100 ml of methanol, and 2.5 g of sodium hydrogen sulfide was added thereto. The resulting solution was stirred at room temperature for 30 minutes and filtered to provide solids, which were washed with 10 ml of distilled water and 10 ml of acetone and dried to obtain 3.1 g of the title compound as a white powder.

m.p.: >210° C.(dec.)

NMR(δ, DMSO-d6): 1.72(m, 4H), 2.08(t, 2H), 2.36(t, 3H), 3.32(s, 3H), 7.12(s, 2H)

Preparation Example 5: Synthesis of paramethoxybenzyl 3-chloromethyl-7-{(Z)-2-[2-(triphenyl-methyl)aminothiazol-4-yl]-2-[(R)-1-diphenylmethoxycarbonylprop-1-oxyimino]acetamido}-3-cephem-4-carboxylate Step 1) Synthesis of S-(−)-2-chlorobutanoic acid A solution of 25.78 g of S-(+)-2-aminobutanoic acid dissolved in 400 ml of 6M HCl solution was cooled to 0° C. and thereto was added dropwise a solution of 27.6 g of sodium nitrite dissolved in 100 ml of distilled water while maintaining below 5° C. The reaction solution was warmed to a room temperature, maintained at that temperature for 18 hours and stirred for additional 3 hours with degassing. Thereto was slowly added 25 g of sodium bicarbonate, and the reaction mixture was extracted four times with 100 ml of ethyl ether.

The separated organic phase was concentrated under a reduced pressure to remove the solvent and the volatile materials. The residues thus obtained were dissolved in 4 ml of saturated sodium chloride solution and the resultant solution was extracted with 30 ml of ethyl ether. The organic layer was dried over calcium chloride and filtered, and the filtrate was distilled at a temperature ranging from 40° to 50° C. under reduced pressure to obtain 17.43 g of the title compound.

NMR(δ, CDCl3): 1.05(t, 3H), 1.88–2.09(m, 2H), 4.27(dd, 1H), 11.35(bs, 1H)

$[\alpha]^{20}_D = -13.07 (c=6.71, \text{methanol})$

Step 2) Synthesis of S-(−)-2-chlorobutanoic benzhydryl ester 16.7 g of S-(−)-2-chlorobutanoic acid obtained in Step 1 was dissolved in 100 ml of diethyl ether and thereto was added dropwise 1M solution of diphenyldiazomethane dissolved in diethyl ether until no generation of nitrogen gas was observed. After the completion of the reaction, 200 ml of 5% sodium bicarbonate solution was added to the reaction solution. The solution was vigorously mixed, and the organic phase separated therefrom was dried over anhydrous magnesium sulfate and filtered. The filtrate was distilled under reduced pressure to remove the solvent, and purified by a silica gel column chromatography to obtain 34 g of the title compound.

NMR(δ, CDCl3): 0.95(t, 3H), 1.87–2.15(m, 2H), 4.30(dd, 1H), 6.90(s, 1H), 7.20–7.40(m, 10H)

$[\alpha]^{20}_D = -6.03 (c=3.17, \text{methanol})$

Step 3) Synthesis of allyl 2-(tritylaminothiazol-4-yl)-2-[(R)-(+)-1-(diphenylmethoxycarbonyl)prop-1-oxyimino]acetate 55.91 g of allyl [2-(tritylamino)thiazol-4-yl]-2-hydroxyiminoacetate and 34 g of the compound obtained in Step 2 were dissolved in 200 ml of dimethyl sulfoxide and thereto was added 32.1 g of potassium carbonate. The resultant solution was stirred for 1.5 hours at 55° C. After completion of the reaction, to the solution was added 500 ml of distilled water and the resultant solution was extracted with 500 ml of diethyl ether. The organic phase was separated, washed with 100 ml of 10% HCl solution and 100 ml of saturated sodium chloride solution, dried over anhydrous magnesium sulfate, filtered, concentrated under reduced pressure to obtain 75.58 g of the title compound.

NMR(δ, CDCl3): 0.92(t, 3H), 1.80–2.00(m, 2H), 4.79(d, 2H), 4.88(dd, 1H), 5.20(d, 1H), 5.38(d, 1H), 5.80–6.00(m, 1H), 6.50(s, 1H), 6.90(s, 1H), 7.17–7.38(m, 26H)

$[\alpha]^{20}_D = +9.87°$ (c=14.35, ethyl acetate)

Step 4) Synthesis of 2-(tritylaminothiazol-4-yl)-2-[(R)-(+)-1-(diphenylmethoxycarbonyl)prop-1-oxyimino]acetic acid To a solution of 75.58 g of the compound obtained in Step 3 dissolved in 500 ml of dichloromethane were added in order 2.75 g of triphenylphosphine, 0.61 g of tetrakis(triphenylphosphine)palladium and a solution of 20.1 g of potassium 2-ethylhexanoate dissolved in 120 ml of ethyl acetate. The resulting mixture were stirred at room temperature for 1 hour. After completion of the reaction, the solution was distilled under reduced pressure to remove the solvent. To the residues were added 500 ml of ethyl acetate and 400 ml of distilled water. The resultant solution was adjusted to pH 2.4 with 10% HCl solution and filtered to collect the solids, which were washed with 500 ml of distilled water and filtered to obtain 64.02 g of the title compound.

NMR($\delta$, DMSO-$d_6$): 0.83(t, 3H), 1.65–1.90(m, 2H), 5.48(dd, 1H), 6.80(s, 1H), 6.83(s, 1H), 7.10–7.50(m, 25H), 8.85(s, 1H), 13.80(bs, 1H)

$[\alpha]^{20}_D = +13.6°$ (C=8.9, dimethylsulfoxide)

Step 5) Synthesis of paramethoxybenzyl 3-chloromethyl-7{(Z)-2-[2-(triphenylmethyl)aminothiazol-4-yl]-2-[(R)-1-diphenylmethoxycarbonylprop-1-oxyimino]acetamido}-3-cephem-4-carboxylate Into 1 l of dichloromethane were charged 86.68 g of paramethoxybenzyl 7-amino-3-chloromethyl-3-cephem-4-carboxylate and 50.64 g of pyridine. The mixture was stirred until it became a complete solution and the solution was cooled to a temperature ranging from −20° C. to −25° C. and thereto were added 135.5 g of the compound obtained in Step 4 and 32.8 g of phosphorous oxychloride. The reaction mixture was stirred for 30 minutes. After completion of the reaction, the mixture was washed with 500 ml of 1% HCl solution. The organic phase was separated therefrom, washed with 500 ml of distilled water and with 500 ml of saturated sodium chloride solution, dried over anhydrous magnesium sulfate and filtered. The filtrate was concentrated under reduced pressure to obtain 185 g of the title compound as an ivory solid.

NMR($\delta$, CDCl$_3$): 1.06(t, 3H), 1.95(q, 2H), 3.29(ABq, 2H), 3.81 (s, 3H), 3.97(ABq, 2H), 4.95(d, 1H), 5.02 (dd, 1H), 5.21(ABq, 2H), 5.92(dd, 1H), 6.72(s, 1H), 6.95(s, 1H), 7.1(ABq, 4H), 7.23–7.41(m, 25H), 8.08(d, 1H)

Preparation Example 6: Synthesis of paramethoxybenzyl 3-chloromethyl-7-{(Z)-2-[2-(triphenylmethyl)aminothiazol-4-yl]-2-[(R,S)-1-diphenylmethoxycarbonylprop-1-oxyimino]acetamido}-3-cephem-4-carboxylate The same procedures described in Steps 2, 3, 4 and 5 of Preparation Example 5 above were repeated except that 17.4 g of (±)-2-bromobutanoic acid was used as a starting material to obtain 185 g of the title compound as a white solid.

NMR($\delta$, CDCl$_3$): 1.02(m, 3H), 1.91(m, 2H), 3.51(ABq, 2H), 3.84 (s, 3H), 4.47(ABq, 2H), 4.74–4.85(m, 1H), 5.02(dd, 1H), 5.20(ABq, 2H), 5.81–6.01(m, 1H), 6.78(s, 1H), 6.92(s, 1H), 6.98(s, 1H), 7.12(ABq, 2H), 7.21–7.38(m, 25H), 8.84(dd, 1H)

Preparation Example 7: Synthesis of paramethoxybenzyl 3-chloromethyl-7{(Z)-2-[2-(triphenylmethyl)aminothiazol-4-yl]-2-[(R,S)-2-diphenylmethoxycarbonylbut-1-oxyimino]acetamido}-3-cephem-4-carboxylate Step 1) Synthsis of allyl 2-(tritylaminothiazol-4-yl)-2-[2-(diphenylmethoxycarbonyl)but-2-oxyimino]acetate To a solution of 250 g of allyl [2-(tritylamino)thiazol-4yl]-2-hydroxyiminoacetate and 200 g of 2-bromo-2-methylbutanoic benzhydryl ester dissolved in 600 ml of dimethyl sulfoxide was added 150 g of potassium carbonate. The resultant solution was stirred at 60° C. for 18 hours, and the solution was poured into a mixture of 3 l of ethyl acetate and 1.5 l of an iced water. The resultant was stirred thoroughly and the organic phase was separated therefrom, washed with 1 l of 1% HCl solution and then with 1 l of saturated sodium chloride solution, dried over magnesium sulfate and filtered. The filtrate was concentrated under reduced pressure to obtain 350 g of the title compound as a white solid.

NMR($\delta$, CDCl$_3$): 0.81(t, 3H), 1.54(s, 3H), 1.91(q, 2H), 4.82 (d, 2H), 5.31(ABq, 2H), 5.86–6.02(m, 1H), 6.47(s, 1H), 6.74(s, 1H), 6.86(s, 1H), 7.12–7.41(m, 25H)

Step 2) Synthesis of 2-(tritylaminothiazol-4-yl)-2-[2-(diphenylmethoxycarbonyl)-but-2-oxyimino]acetic acid 350 g of the compound obtained in Step 1 above was dissolved in 1.4 l of dichloromethane and thereto were added in order 17.2 g of triphenylphosphine, 3.05 g of tetrakis (triphenylphosphine)palladium and a solution of 95.25 g of potassium 2-ethylhexanoate dissolved in 600 ml of ethyl acetate. The solution was stirred at room temperature for 4 hours. The solution was distilled under reduced pressure to obtain residues to which were added a mixture of 600 ml of ethyl acetate and 600 ml of distilled water. The resultant solution was adjusted to about pH 2.8 with 5% HCl solution and the organic phase was separated therefrom, dried over anhydrous magnesium sulfate and filtered. The filtrate was distilled under reduced pressure to obtain residues, which were purified by a silicagel column choamatography to obtain 280 g of the title compound as a white solid.

NMR($\delta$, CDCl$_3$): 0.72(t, 3H), 1.57(s, 3H), 1.87(q, 2H), 6.33 (s, 1H), 6.90(S, 1H), 7.14–7.42(m, 26H), 9.02(bs, 1H)

Step 3) Synthesis of paramethoxylbenzyl 3-chloromethyl-7{(Z)-2-[2-(triphenylmethyl)aminothiazol-4-yl]-2-[(R,S)-2-diphenylmethoxycarbonylbut-1-oxyimino]acetamido}-3-cephem-4-carboxylate Into 1 l of dichloromethane were charged 86.7 g of parmethoxybenzyl 7-amino-3-chloromethyl-3-cephem-4-carboxylate and 50.64 g of pyridine. After the mixture was stirred until it became a complete solution, the solution was cooled to a temperature ranging from −20° to −25° C. and 135.5 g of the compound obtained in Step 2 and 32.8 g of phosphorous oxychloride were added thereto. The reaction mixture was stirred for 30 minutes. After completion of the reaction, the mixture was washed with 500 ml of 1% HCl solution and the organic phase was separated therefrom, washed with 500 ml of distilled water and then 500 ml of saturated sodium chloride solution, dried over anhydrous magnesium sulfate and filtered. The filtrate was concentrated under a reduced pressure to obtain 185 g of the title compound as an ivory solid.

NMR($\delta$, CDCl$_3$): 0.85–0.89(m, 3H), 1.69(d, 3H), 1.87–2.24 (m, 2H), 3.08–3.17(m, 2H), 3.85(s, 3H), 4.44–4.61 (m, 2H), 5.02 (dd, 1H) , 5.20–5.36 (m, 2H), 5.89–6.01(m, 1H), 6.67(d, 1H), 6.91(d, 1H), 6.97(d, 1H), 7.15–7.45(m, 29H)

Example 1: Synthesis of 7-[(Z)-2-(2-aminothiazol-4-yl)-2-(2-carboxyprop-2-oxyimino)acetamido]-3-(1,4- diamino-1,5,6,7-tetrahydro-cyclopentapyrimidinium-2-yl)thiomethyl-3-cephem-4-carboxylate(I-1)

To a solution of 2.0 g of paramethoxybenzyl 3-chloromethyl-7-[(Z)-2-(2-tert-butoxycarbonylprop-2-oxyimino)2-{2-(triphenylmethyl)aminothiazol-4-yl}acetamido]-3-cephem-4-carboxylate dissolved in 10 ml of dimethylsulfoxde(DMSO) was added 380 mg of 1,4-diamino-1,5,6,7-tetrahydro-cyclopenta-pyrimidine-2-thione synthesized in Preparation Example 1 above and the reaction solution was stirred at room temperature for 2 hours. To the reaction solution was added 50 ml of diethyl ether and the resulting solution was distilled under reduced pressure to remove the ether solvent. The residue so obtained was dissolved in 20 ml of $CH_2Cl_2$ and the resultant solution was added slowly to 100 ml of ethyl ether to produce precipitates, which were collected by filtration, washed with 50 ml of ethyl ether and dried. The dried solids were dissolved in 10 ml of phenol, and 1.0 ml of c-HCl was added thereto. The resulting solution was stirred at 50° C. for 2 hours and cooled to room temperature, and 100 ml of acetone was added thereto to produce precipitates, which were collected by filtration, washed with 40 ml of acetone and dried to obtain 1.3 g of ivory solids. The solids were purified by a fractional liquid chromatography($\mu$-Bondapak $C_{18}$ steel column: 19 mm×30 cm) using as an eluent a 10% methanol solution to obtain 700 mg of the title compound as a white solid.

MS(FAB, M+1): 650

NMR($\delta$, $D_2O$+$NaHCO_3$): 1.56(d, 6H), 2.27(m, 2H), 2.82(t, 3H), 3.15(t, 2H), 3.60(ABq, 2H), 4.28 (ABq, 2H), 5.16(d, 1H), 5.80(d, 1H), 6.98(s, 1H)

IR(KBr, $cm^{-1}$): 1760($\beta$-lactam), 1680, 1620, 1560

Example 2: Synthesis of 7-[(Z)-2-(2-aminothiazol-4-yl)-2-(2-carboxyprop-2-oxyimino)acetamido]-3-(4-amino-1-methyl-1,5,6,7-tetrahydro-cyclopentapyrimidinium-2-yl)thiomethyl-3-cephem-4-carboxylate(I-2)

The same procedures as described in Example 1 above were repeated except that 180 mg of 4-amino-1-methyl-1,5,6,7-tetrahydro-cyclopentapyrimidine-2-thione synthesized in Preparation Example 2 above was used as a starting material to obtain 670 mg of the title compound as a white powder.

MS(FAB, M+1): 649

NMR($\delta$, $D_2O$+$NaHCO_3$): 1.55(d, 6H), 2.26(m, 2H), 2.78(t, 2H), 3.08(t, 2H), 3.58(ABq, 2H), 3.68(s, 3H), 4.32(ABq, 2H), 5.16(d, 1H), 5.78(d, 1H), 6.94(s, 1H)

IR(KBr, $cm^{-1}$): 1765($\beta$-lactam), 1690, 1630, 1570

Example 3: Synthesis of 7-[(Z)-2-(2-aminothiazol-4-yl)-2-(2-carboxyprop-2-oxyimino)acetamido]-3-(1,4-diamino-5,6,7,8-tetrahydro-1H-quinazolinium-2-yl) thiomethyl-3-cephem-4-carboxylate(I-3)

The same procedures as described in Example 1 above were repeated except that 190 mg of 1,4-diamino-5,6,7,8-tetrahydro-1H-quinazoline-2-thione synthesized in preparation Example 3 above was used as a starting material to obtain 680 mg of the title compound as a white powder.

MS(FAB, M+1): 664

NMR($\delta$, $D_2O$+$NaHCO_3$): 1.52(d, 6H), 1.62(m, 4H), 1.93(t, 2H), 2.43(t, 2S), 3.52(ABq, 2H), 4.35 (ABq, 2H), 5.18(d, 1H), 5.85(d, 1H), 6.98(s, 1H)

IR(KBr, $cm^{-1}$): 1768($\beta$-lactam), 1670, 1620, 1550

Example 4: Synthesis of 7-[(Z)-2-(2-aminothiazol-4-yl)-2-(2-carboxyprop-2-oxyimino)acetamido]-3-(4-amino-1-methyl-5,6,7,8-tetrahydro-1H-quinazolinium-2-yl) thiomethyl-3-cephem-4-carboxylate(I-4)

The same procedures as described in Example 1 above were repeated except that 190 mg of 4-amino-1-methyl-5,6,7,8-tetrahydro-1H-quinazoline-2-thione synthesized in Preparation Example 4 above was used as a starting material to obtain 670 mg of the title compound as a white powder.

MS(FAB, M+1): 663

NMR($\delta$, $D_2O$+$NaHCO_3$): 1.54(d, 6H), 1.60(m, 4H), 1.88(t, 2H), 2.26(t, 2H), 3.52(s, 3H), 3.61(s, 3H), 4.33(ABq, 2H), 5.15(d, 1H), 5.76(d, 1H), 7.00(s, 1H)

IR(KBr, $cm^{-1}$): 1760($\beta$-lactam), 1670, 1590, 1525

Example 5: Synthesis of 7-[(Z)-2-(2-aminothiazol-4-yl)-2-((S)-1-carboxyeth-1-oxyimino)acetamido]-3-(1,4-diamino-1,5,6,7-tetrahydro-cyclopentapyrimidinium-2-yl)thiomethyl-3-cephem-4-carboxylate(I-5(S))

To a solution of 2.0 g of paramethoxybenzyl 3-chloromethyl-7-[(Z)-2-(S)-1-tert-butoxycarbonyleth-1-oxyimino)-2-{2-(triphenylmethyl)aminothiazol-4-yl}acetamido]-3-cephem-4-carboxylate dissolved in 10 ml of DMSO was added 380 mg of 1,4-diamino-1,5,6,7-tetrahydro-cyclopentapyrimidine-2-thione synthesized in Preparation Example 1 above and the reaction solution was stirred at room temperature for 3 hours. To the reaction solution was added 50 ml of diethyl ether and the resulting solution was distilled under reduced pressure to remove the ether solvent. The residues so obtained was dissolved in 20 ml of $CH_2Cl_2$ and the resultant solution was added slowly to 100 ml of ethyl ether to produce precipitates, which were collected by filtration, washed with 50 ml of diethyl ether and dried. The dried solids were dissolved in 2 ml of phenol, and 1.0 ml of c-HCl was added thereto. The resulting solution was stirred at 50° C. for 2 hours and cooled to room temperature, and 100 ml of acetone was added thereto to produce precipitates, which were collected by filtration, washed with 50 ml of acetone and dried to obtain 1.2 g of an ivory solids. The solids were purified by a fractional liquid chromatography($\mu$-Bondapak $C_{18}$ steel column: 19 mm×30 cm) using as an eluent a 5% methanol solution to obtain 550 mg of the title compound as a white solid.

MS(FAB, M+1): 636

NMR($\delta$, $D_2O$+$NaHCO_3$): 1.49(d, 3H), 2.22(m, 2H), 2.76(t, 2H), 3.0S(t, 2H), 3.59(ABq, 2H), 4.29 (ABq, 2H), 4.70(ABq, 2H), 5.18(d, 1H), 5.74(d, 1H), 6.95(s, 1H)

IR(KBr, $cm^{-1}$): 1750 ($\beta$-lactam) , 1680, 1600, 1530

Example 6: Synthesis of 7-[(Z)-2-(2-aminothiazol-4-yl}-2-((S-1-carboxyeth-1-oxyimino)acetamido]-3-(4-amino-1-methyl-1,5,6,7-tetrahydro-cyclopentapyrimidinium-2-yl)thiomethyl-3-cephem-4-carboxylate(I-6(S))

The same procedures as described in Example 5 above were repeated except that 300 mg of 4-amino-1-methyl-1,5,6,7-tetrahydro-cyclopentapyrimidine-2-thione synthesized in preparation Example 2 above was used as a starting material to obtain 250 mg of the title compound as a white powder.

MS(FAB, M+1): 635

NMR($\delta$, $D_2O$+$NaHCO_3$): 1.46(d, 3H), 2.23(m, 2H), 2.68(t, 2H), 3.04(t, 2H), 3.48(ASq, 2H), 3.64(s, 3H), 4.31(ASq, 2H), 4.65(q, 1H), 5.18(d, 1H), 5.78(d, 1H), 6.98(s, 1H)

IR(KBr, $cm^{-1}$): 1765($\beta$-lactam), 1670, 1600, 1520

Example 7: Synthesis of 7-[(Z)-2-(2-aminothiazol-4-yl}-2-((S)-1-carboxyeth-1-oxyimino)acetamido]-3-(1,4-diamino-5,6,7,8-tetrahydro-1H-quinazolinium-2-yl) thiomethyl-3-cephem-4-carboxylate(I-7(S))

The same procedures as described in Example 5 above were repeated except that 310 mg of 1,4-diamino-5,6,7,8-tetrahydro-1H-quinazoline-2-thione synthesized in Preparation Example 3 above was used as a starting material to obtain 260 mg of the title compound as a white powder.

MS(FAB, M+1): 650
NMR(δ, D$_2$O+NaHCO$_3$): 1.47(d, 3H), 1.64(m, 4H), 2.02(t, 2H), 2.45(t, 2H), 3.56(ABq, 2H), 4.27 (ABq, 2H), 4.72(q, 1H), 5.09(d, 1H), 5.76(d, 1H), 6.98(s, 1H)
IR(KBr, cm$^{-1}$): 1770(β-lactam), 1680, 1615, 1570

Example 8: Synthesis of 7-[(Z)-2-(2-aminothiazol-4-yl)-2-(1-carboxymeth-1-oxyimino)acetamido]-3-(1,4-diamino-1,5,6,7-tetrahydro-cyclopentapyrimidinium-2-yl)thiomethyl-3-cephem-4-carboxylate(I-8)

To a solution of 2.0 g of paramethoxybenzyl 3-chloromethyl-7-[(Z)-2-(tert-butoxycarbonylmethoxyimino)-2-{2-(triphenylmethyl)aminothiazol-4-yl}acetamido]-3-cephem-4-carboxylate dissolved in 10 ml of DMSO was added 400 mg of 1,4-diamino-1,5,6,7-tetrahydro-cyclopentapyrimidine-2-thione synthesized in Preparation Example 1 above and the reaction solution was stirred at room temperature for 2 hours. To the reaction solution was added 50 ml of diethyl ether and the resulting solution was stirred vigorously and distilled under reduced pressure to remove the ether solvent. The residues so obtained was dissolved in 20 ml of CH$_2$Cl$_2$ and the resultant solution was added slowly to 100 ml of ethyl ether to produce precipitates, which were collected by filtration, washed with 50 ml of diethyl ether and dried. The dried solids were dissolved in 10 ml of phenol, and 1.0 ml of c-HCl was added thereto. The resulting solution was stirred at 50° C. for 2 hours and cooled to room temperature, and 100 ml of acetone was added thereto to produce precipitates, which were collected by filtration, washed with 40 ml of acetone and dried to obtain 1.2 g of an ivory solids. The solids were purified by a fractional liquid chromatography (μ-Bondapak C$_{18}$ steel column: 19 mm×30 cm) using as an eluent a 10% methanol solution to obtain 680 mg of the title compound as a white solid.

MS(FAB, M+1): 622
NMR(δ, D$_2$O+NaHCO$_3$): 2.22(m, 4H), 2.81(m, 2H), 3.12(t, 2H), 3.57(ABq, 2H), 4.34(ABq, 2H), 4.83 (s, 2H), 5.16(d, 1H), 5.78(d, 1H), 6.99(s, 1H)
IR(KBr, cm$^{-1}$): 1765(β-lactam), 1685, 1665, 1530

Example 9: Synthesis of 7-[(Z)-2-(2-aminothiazol-4-yl}-2-(1-carboxymeth-1-oxyimino)acetamido]-3-(4-amino-1-methyl-1,5,6,7-tetrahydro-cyclopentapyrimidinium-2-yl)thiomethyl-3-cephem-4-carboxylate(I-9)

The same procedures as described in Example 8 above were repeated except that 400 mg of 4-amino-1-methyl-1,5,6,7-tetrahydro-cyclopentapyrimidine-2-thione synthesized in Preparation Example 2 above was used as a starting material to obtain 650 mg of the title compound as a white powder.

MS(FAB, M+1): 621
NMR(δ, D$_2$O+NaHCO$_3$): 2.24(m, 2H), 2.76(t, 2H), 3.04(t, 2H), 3.56(ABq, 2H), 3.65(s, 3H), 4.36 (ABq, 1H), 4.81(s, 2H), 5.17(d, 1H), 5.80(d, 1H), 6.96(s, 1H)
IR(KBr, cm$^{-1}$): 1760(β-lactam), 1680, 1610, 1580

Example 10: Synthesis of 7-[(Z)-2-(2-aminothiazol-4-yl)-2-(methoxyimino)acetamido]-3-(1,4-diamino-1,5,6,7-tetrahydro-cyclopentapyrimidinium-2-yl)thiomethyl-3-cephem-4-carboxylate(I-10)

To a solution of 2.0 g of paramethoxybenzyl 3-chloromethyl-7-[(Z)-2-(methoxyimino)-2-{2-(triphenylmethyl)aminothiazol-4-yl}acetamido]-3-cephem-4-carboxylate dissolved in 10 ml of DMSO was added 420 mg of 1,4-diamino-1,5,6,7-tetrahydro-cyclopentapyrimidine- 2-thione synthesized in Preparation Example 1 above and the reaction solution was stirred at room temperature for 2 hours. The reaction solution was extracted with a mixture of 30 ml of tetrahydrofuran and 30 ml of ethyl acetate, and washed with 100 ml of saturated sodium chloride solution. The organic layer was dried over anhydrous magnesium sulfate and distilled under reduced pressure to remove the solvent. The residues so obtained was dissolved in 4 ml of anisole and the resultant solution was cooled to a temperature ranging from 0° to 4° C. Thereto was added 8 ml of trifluoroacetic acid and the resulting solution was stirred at room temperature for 50 minutes and cooled to a temperature ranging from −20° to −30° C., and 50 ml of diethyl ether was added thereto to produce precipitates, which were collected by filtration, washed with 40 ml of acetone and dried to obtain 1.2 g of ivory solids. The solids were purified by a fractional liquid chromatography (μ-Bondapak C$_{18}$ steel column: 19 mm×30 cm) using as an eluent a 20% methanol solution to obtain 700 mg of the title compound as a white solid.

MS(FAB, M+1): 578
NMR(δ, D$_2$O+NaHCO$_3$): 2.22(m, 2H), 2.85(t, 2H), 3.12(t, 2H), 3.61(ABq, 2H), 3.79(s, 3H), 4.39 (ABq, 1H), 5.16(d, 1H), 5.72(d, 1H), 6.94(s, 1H)
IR(KBr, cm$^{-1}$): 1765(β-lactam), 1700, 1640, 1580

Example 11: Synthesis of 7-[(Z)-2-(2-aminothiazol-4-yl)-2-(1-carboxycyclopent-1-oxyimino)acetamido]-3-(1,4-diamino-1,5,6,7-tetrahydro-cyclopentapyrimidinium-2-yl)thiomethyl-3-cephem-4-carboxylate(I-11)

To a solution of 2.0 g of paramethoxybenzyl 3-chloromethyl-7-[(Z)-2-(1-diphenylmethoxycarbonyl)-cyclopent-1-oxyimino)-2-{2-(triphenylmethyl)aminothiazol-4-yl}acetamido]-3-cephem-4-carboxylate dissolved in 10 ml of DMSO was added 410 mg of 1,4-diamino-1,5,6,7-tetrahydro-cyclopentapyrimidine-2-thione synthesized in Preparation Example 1 above and the reaction solution was stirred at room temperature for 2 hours. The reaction solution was extracted with a mixture of 30 ml of tetrahydrofuran and 30 ml of ethyl acetate, and washed with 100 ml of saturated sodium chloride solution. The organic layer was dried over anhydrous magnesium sulfate and distilled under reduced pressure to remove the solvent. The residues so obtained was dissolved in 4 ml of anisole and the resultant solution was cooled to a temperature ranging from 0° to 4° C. Thereto was added 8 ml of trifluoroacetic acid and the resulting solution was stirred at room temperature for 50 minutes and cooled to a temperature ranging from −20° to −30° C., and 50 ml of diethyl ether was added thereto to produce precipitates, which were collected by filtration, washed with 40 ml of acetone and dried to obtain 1.2 g of ivory solids. The solids were purified by a fractional liquid chromatography (μ-Bondapak C$_{18}$ steel column: 19 mm×30 cm) using as an eluent a 20% methanol solution to obtain 700 mg of the title compound as a white solid.

MS(FAB, M+1): 675
NMR(δ, D$_2$O+NaHCO$_3$): 1.73(m, 4H), 2.09(m, 4H), 2.24(m, 2H), 2.81 t, 2H), 3.12(t, 2H), 3.57 (ABq, 2H), 4.36(ABq, 2H), 5.15(d, 1H), 5.76(d, 1H), 7.00(s, 1H)
IR(KBr, cm$^{-1}$): 1765 (β-lactam), 1765, 1580, 1520

Example 12: Synthesis of 7-[(Z)-2-(2-aminothiazol-4-yl}-2-(1-carboxycyclopent-1-oxyimino)acetamido]-3-

(4-amino-1-methyl-1,5,6,7-tetrahydro-cyclopentapyrimidinium-2-yl)thiomethyl-3-cephem-4-carboxylate(I-12)

The same procedures as described in Example 11 above were repeated except that 400 mg of 4-amino-1-methyl-1,5,6,7-tetrahydro-cyclopentapyrimidine-2-thione synthesized in Preparation Example 2 above was used as a starting material to obtain 650 mg of the title compound as a white powder.

MS(FAB, M+1): 675

NMR($\delta$, $D_2O$+$NaHCO_3$): 1.72(m, 4H), 2.11(m, 4H), 2.26(m, 2H), 2.79(t, 2H), 3.06(t, 2H), 3.58(ABq, 2H), 3.69(s, 3H), 4.51(ABq, 2H), 5.16(d, 1H), 5.80(d, 1H), 6.99(s, 1H)

IR(KBr, $cm^{-1}$): 1760($\beta$-lactam), 1670, 1590, 1525

Example 13: Synthesis of 7-[(Z)-2-(2-aminothiazol-4-yl)-2-((S)-1-carboxyprop-1-oxyimino)acetamido]-3-(1,4-diamino-1,5,6,7-tetrahydro-cyclopentapyrimidinium-2-yl)thiomethyl-3-cephem-4-carboxylate(I-13(S))

To a solution of 1.5 g of paramethoxybenzyl 3-chloromethyl-7-[(Z)-2-(1-diphenylmethoxycarbonyl-prop-1-oxyimino)-2-{2-(triphenylmethyl)aminothiazol-4-yl}acetamido]-3-cephem-4-carboxylate dissolved in 10 ml of DMSO was added 350 mg of 1,4-diamino-1,5,6,7-tetrahydro-cyclopenta-pyrimidine-2-thione synthesized in Preparation Example 1 above and the reaction solution was stirred at room temperature for 3 hours. The reaction solution was extracted with a mixture of 20 ml of tetrahydrofuran and 20 ml of ethyl acetate, and washed with 100 ml of saturated sodium chloride solution. The organic layer was dried over anhydrous magnesium sulfate and distilled under reduced pressure to remove the solvent. The residues so obtained was dissolved in 4 ml of anisole and the resultant solution was cooled to a temperature ranging from 0° to 4° C. Thereto was added 8 ml of trifluoroacetic acid and the resulting solution was stirred at room temperature for 40 minutes and cooled to a temperature ranging from −20° to −30° C., and 50 ml of diethyl ether was added thereto to produce precipitates, which were collected by filtration, washed with 50 ml of acetone and dried to obtain 0.9 g of ivory solids. The solids were purified by a fractional liquid chromatography($\beta$-Bondapak $C_{18}$ steel column: 19 mm×30 cm) using as an eluent a 25% methanol solution to obtain 500 mg of the title compound as a white solid.

MS(FAB, M+1): 650

NMR($\delta$, $D_2O$+$NaHCO_3$): 0.93(t, 3H), 1.76(q, 2H), 2.24(m, 2H), 2.76(t, 2H), 3.06(t, 2H), 3.57 (ABq, 2H), 4.36(ABq, 2H), 4.63(ABq, 1H), 5.15 (d, 1H), 5.78(d, 1H), 6.76(s, 1H)

IR(KBr, $cm^{-1}$): 1765($\beta$-lactam), 1670, 1610, 1520

Example 14: Synthesis of 7-[(Z)-2-(2-aminothiazol-4-yl}-2-((S)-1-carboxyprop-1-oxyimino)acetamido]-3-(4-amino-1-methyl-1,5,6,7-tetrahydro-cyclopentapyrimidinium-2-yl)thiomethyl-3-cephem-4-carboxylate(I-14(S))

The same procedures as described in Example 13 above were repeated except that 320 mg of 4-amino-1-methyl-1,5,6,7-tetrahydro-cyclopentapyrimidine-2-thione synthesized in Preparation Example 2 above was used as a starting material to obtain 520 mg of the title compound as a white powder.

MS(FAB, M+1): 649

NMR($\delta$, $D_2O$+$NaHCO_3$): 0.94(t, 3H), 1.82(q, 2H), 2.23(m, 2H), 2.81(t, 2H), 3.12(t, 2H), 3.58(ABq, 2H), 3.64(s, 3H), 4.33(ABq, 2H), 4.66(q, 1H), 5.18(d, 1H), 5.78(d, 1H), 6.99(s, 1H)

IR(KBr, $cm^{-1}$): 1765($\beta$-lactam), 1660, 1590, 1530

Example 15: Synthesis of 7-[(Z)-2-(2-aminothiazol-4-yl )-2-(2-carboxybut-2-oxyimino)acetamido]-3-(1,4-diamino-1,5,6,7-tetrahydro-cyclopentapyrimidinium-2-yl)thiomethyl-3-cephem-4-carboxylate(I-15(S) and I-15(R))

To a solution of 2.0 g of paramethoxybenzyl 3-chloromethyl-7-[(Z)-2-diphenylmethoxycarbonylbut-2-oxyimino)-2-{2-(triphenylmethyl)aminothiazol-4-yl}acetamido]-3-cephem-4-carboxylate dissolved in 10 ml of DMSO was added 380 mg of 1,4-diamino-1,5,6,7-tetrahydro-cyclopentapyrimidine-2-thione synthesized in Preparation Example 1 above and the reaction solution was stirred at room temperature for 2 hours. To the reaction solution was added 50 ml of diethyl ether and the resulting solution was stirred vigorously and distilled under reduced pressure to remove the ether solvent. The residues so obtained were dissolved in 20 ml of $CH_2Cl_2$ and the resultant solution was added slowly to 100 ml of ethyl ether to produce precipitates, which were collected by filtration, washed with 50 ml of diethyl ether and dried. The dried solids were dissolved in 4 ml of anisole and the resulting solution was cooled to a temperature ranging from 0° to 4° C. Thereto was added 8 ml of trifluoroacetic acid and the resulting solution was stirred at room temperature for 50 minutes and cooled to a temperature ranging from −20° to −30° C., and 50 ml of diethyl ether was added thereto to produce precipitates, which were collected by filtration, washed with 40 ml of acetone and dried to obtain 1.1 g of ivory solids. The solids were purified by a fractional liquid chromatography($\mu$-Bondapak $C_{18}$ steel column: 19 mm×30 cm) using as an eluent a 15% methanol solution to obtain 200 mg and 220 mg of the title compound as a S-isomer and R-isomer, respectively.

MS(FAB, M+1): 664

NMR($\delta$, $D_2O$+$NaHCO_3$):

S-isomer: 0.88(t, 3H) 1.49(s, 3H), 1.88(q, 2H), 2.23(m, 2H), 2.81(t, 2H), 3.11(t, 2H), 3.57(ABq, 2H), 3.86 (ABq, 2H), 5.16(d, 1H), 5.81(d, 1H), 6.99(s, 1H)

R-isomer: 0.91(t, 3H), 1.44(5, 3H), 1.88(q, 2H), 2.22(m, 2H), 2.81(t, 2H), 3.10(t, 2H), 3.56(ABq, 2H), 5.13 (d, 1H), 5.74(d, 1H), 6.98(s, 1H)

IR(KBr, $cm^{-1}$): 1765($\beta$-lactam), 1670, 1600, 1520

Example 16: Synthesis of 7-[(Z)-2-(2-aminothiazol-4-yl}-2-(2-carboxybut-2-oxyimino)acetamido]-3-(4-amino-1-methyl-1,5,6,7-tetrahydro-cyclopentapyrimidinium-2-yl)thiomethyl-3-cephem-4-carboxylate(I-16(S) and I-16(R))

The same procedures as described in Example 15 above were repeated except that 350 mg of 4-amino-1-methyl-1,5,6,7-tetrahydro-cyclopentapyrimidine-2-thione synthesized in preparation Example 2 above was used as a starting material to obtain 230 mg and 220 mg of the title compound as a S-isomer and R-isomer, respectively.

MS(FAB, M+1): 663

NMR($\delta$, $D_2O$+$NaHCO_3$):

S-isomer: 0.86(t, 3H), 1.51(s, 3H), 2.24(m, 2H), 2.84(t, 2H), 3.12(t, 2H), 3.61(ABq, 2H), 3.63(s, 3H), 4.23 (ABq, 2H), 5.15(d, 1H), 5.76(d, 1H), 6.95(s, 1H)

R-isomer: 0.87(t, 3H), 1.52(s, 3H), 2.25(m, 2H), 2.84(t, 3H), 3.14(t, 2H), 3.62(ABq, 2H), 3.67(s, 3H), 4.25 (ABq, 2H), 5.14(d, 1H), 5.77(d, 1H), 6.95(s, 1H)

IR(KBr, $cm^{-1}$): 1765($\beta$-lactam), 1680, 1620, 1530

Example 17: Synthesis of 7-[(Z)-2-(2-aminothiazol-4-yl)-2-(ethoxyimino)acetamido]-3-(1,4-diamino-1,5,6,7- tetrahydro-cyclopentapyrimidinium-2-yl)thiomethyl-3-cephem-4-carboxylate(I-17)

To a solution of 2.0 g of paramethoxybenzyl 3-chloromethyl-7-[(Z)-2-(ethoxyimino)-2-{2-(triphenylmethyl)aminothiazol-4-yl}acetamido]-3-cephem-4-carboxylate dissolved in 10 ml of DMSO was added 420 mg of 1,4-diamino-1,5,6,7-tetrahydro-cyclopentapyrimidine-2-thione synthesized in Preparation Example 1 above and the reaction solution was stirred at room temperature for 2 hours. The reaction solution was extracted with a mixture of 30 ml of tetrahydrofuran and 30 ml of ethyl acetate, and washed with 100 ml of saturated sodium chloride solution. The organic layer was dried over anhydrous magnesium sulfate and distilled under reduced pressure to remove the solvent. The residues so obtained was dissolved in 4 ml of anisole and the resultant solution was cooled to a temperature ranging from 0° to 4° C. Thereto was added 8 ml of trifluoroacetic acid and the resulting solution was stirred at room temperature for 50 minutes and cooled to a temperature ranging from −20° to −30° C., and 50 ml of diethyl ether was added thereto to produce precipitates, which were collected by filtration, washed with 40 ml of acetone and dried to obtain 1.2 g of ivory solids. The solids were purified by a fractional liquid chromatography($\mu$-Bondapak $C_{18}$ steel column: 19 mm × 30 cm) using as an eluent a 20% methanol solution to obtain 680 mg of the title compound as a white solid.

MS(FAB, M+1): 592

NMR($\delta$, $D_2O$+$NaHCO_3$): 1.29(t, 3H), 2.23(m, 2H), 2.85(t, 2H), 3.13(t, 2H), 3.61(ABq, 2H), 4.25(q, 2H), 4.40(ABq, 1H), 5.10(d, 1H), 5.72(d, 1H), 6.94(s, 1H)

IR(KBr, $cm^{-1}$): 1765($\beta$-lactam), 1705, 1650, 1590

Example 18: Synthesis of 7-[(Z)-2-(2-aminothiazol-4-yl}-2-(ethoxyimino)acetamido]-3-(1,4-diamino-5,6,7,8-tetrahydro-1H-quinazolinium-2-yl)thiomethyl-3-cephem-4-carboxylate(I-18)

The same procedures as described in Example 17 above were repeated except that 190 mg of 1,4-diamino-5,6,7,8-tetrahydro-1H-quinazoline-2-thione synthesized in Preparation Example 3 above was used as a starting material to obtain 680 mg of the title compound as a white powder.

MS(FAB, M+1): 606

NMR($\delta$, $D_2O$+$NaHCO_3$): 1.30(t, 2H), 1.62(m, 4H), 1.93(t, 2H), 2.43(t, 2H), 3.52(ABq, 2H), 4.25 (q, 2H), 4.35(ABq, 2H), 5.18(d, 1H), 5.85(d, 1H), 6.98(s, 1H)

IR(KBr, $cm^{-1}$): 1768($\beta$-lactam), 1670, 1620, 1550

Example 19: Synthesis of 7-[(Z)-2-(2-aminothiazol-4-yl}-2-(ethoxyimino)acetamido]-3-(4-amino-1-methyl-1,5,6,7-tetrahydro-cyclopentapyrimidinium-2-yl) thiomethyl-3-cephem-4-carboxylate(I-19)

The same procedures as described in Example 17 above were repeated except that 180 mg of 4-amino-1-methyl-1,5,6,7-tetrahydro-cyclopentapyrimidine-2-thione synthesized in Preparation Example 2 above was used as a starting material to obtain 670 mg of the title compound as a white powder.

MS(FAB, M+1): 591

NMR($\delta$, $D_2O$+$NaHCO_3$): 1.29(t, 2H), 2.26(m, 2H), 2.78(t, 2H), 3.08(t, 2H), 3.58(ABq, 2H), 3.68(s, 3H), 4.21(q, 2H), 4.32(ABq, 2H), 5.16(d, 1H), 5.78(d, 1H), 6.94(s, 1H)

IR(KBr, $cm^{-1}$): 1765($\beta$-lactam), 1690, 1630, 1570

Example 20 Synthesis-of 7-[(Z)-2-(2-aminothiazol-4-yl)-2-((R)-1-carboxyeth-1-oxyimino)acetamido]-3-(1,4-diamino-1,5,6,7-tetrahydro-cyclopentapyrimidinium-2-yl)thiomethyl-3-cephem-4-carboxylate(I-5(R))

To a solution of 2.0 g of paramethoxybenzyl 3-chloromethyl-7-[(Z)-2-(1-tert-butoxycarbonyleth-1-oxyimino)-2-{2-(triphenylmethyl)aminothiazol-4-yl}acetamido]-3-cephem-4carboxylate dissolved in 10 ml of DMSO was added 380 mg of 1,4-diamino-1,5,6,7-tetrahydro-cyclopentapyrimidine-2-thione synthesized in Preparation Example 1 above and the reaction solution was stirred at room temperature for 3 hours. To the reaction solution was added 50 ml of diethyl ether and the resulting solution was distilled under reduced pressure to remove the ether solvent. The residues so obtained was dissolved in 20 ml of $CH_2Cl_2$ and the resultant solution was added slowly to 100 ml of ethyl ether to produce precipitates, which were collected by filtration, washed with 50 ml of diethyl ether and dried. The dried solids were dissolved in 2 ml of phenol, and 1.0 ml of c-HCl was added thereto. The resulting solution was stirred at 50° C. for 2 hours and cooled to room temperature, and 100 ml of acetone was added thereto to produce precipitates, which were collected by filtration, washed with 50 ml of acetone and dried to obtain 1.2 g of an ivory solids. The solids were purified by a fractional liquid chromatography($\mu$-Bondapak $C_{18}$ steel column: 19 mm × 30 cm) using as an eluent a 5% methanol solution to obtain 550 mg of the title compound as a white solid.

MS(FAB, M+1): 636

NMR($\delta$, $D_2O$+$NaHCO_3$): 1.48(d, 3H), 2.22(m, 2H), 2.74(t, 2H), 3.08(t, 2H), 3.63(ABq, 2H), 4.32 (ABq, 2H), 4.70(ABq, 2H), 5.19(d, 1H), 5.74(d, 1H), 6.96(s, 1H)

IR(KBr, $cm^{-1}$): 1750($\beta$-lactam), 1680, 1600, 1530

Example 21: Synthesis of 7-[(Z)-2-(2-aminothiazol-4-yl}-2-((R)-1-carboxyeth-1-oxyimino)acetamido]-3-(4-amino-1-methyl-1,5,6,7-tetrahydro-cyclopentapyrimidinium-2-yl)thiomethyl-3-cephem-4-carboxylate(I-6(R))

The same procedures as described in Example 20 above were repeated except that 300 mg of 4-amino-1-methyl-1,5,6,7-tetrahydro-cyclopentapyrimidine-2-thione synthesized in Preparation Example 2 above was used as a starting material to obtain 255 mg of the title compound as a white powder.

MS(FAB, M+1): 635

NMR($\delta$, $D_2O$+$NaHCO_3$): 1.47(d, 3H), 2.23(m, 2H), 2.69 (t, 2H) , 3.04(t, 2H), 3.50(ABq, 2H), 3.64(s, 3H), 4.34(ABq, 2H), 4.65(q, 1H), 5.19(d, 1H), 5.78(d, 1H), 6.99(s, 1H)

IR(KBr, $cm^{-1}$): 1765($\beta$-lactam), 1670, 1600, 1520

Example 22: Synthesis of 7-[(Z)-2-(2-aminothiazol-4-yl}-2-((R)-1-carboxyeth-1-oxyimino)acetamido]-3-(1,4-diamino-5,6,7,8-tetrahydro-1H-quinazolinium-2-yl) thiomethyl-3-cephem-4-carboxylate(I-7(R))

The same procedures as described in Example 20 above were repeated except that 310 mg of 1,4-diamino-5,6,7,8-tetrahydro-1H-quinazoline-2-thione synthesized in Preparation Example 3 above was used as a starting material to obtain 265 mg of the title compound as a white powder.

MS(FAB, M+1): 650

NMR($\delta$, $D_2O$+$NaHCO_3$): 1.48(d, 3H), 1.64(m, 4H), 2.04(t, 2H), 2.45(t, 2H), 3.58(ABq, 2H), 4.31 (ABq, 2H), 4.72(q, 1H), 5.12(d, 1H), 5.76(d, 1H), 6.99(s, 1H)

IR(KBr, $cm^{-1}$): 1770($\beta$-lactam), 1680, 1615, 1570

Example 23: Synthesis of 7-[(Z)-2-(2-aminothiazol-4-yl)-2-((R)-1-carboxyprop-1-oxyimino)acetamido]-3-

(1,4-diamino-1,5,6,7-tetrahydro-cyclopentapyrimidinium-2-yl)thiomethyl-3-cephem-4-carboxylate(I-13(R))

To a solution of 1.5 g of paramethoxybenzyl 3-chloromethyl-7-[(Z)-2-((R)-1-diphenylmethoxycarbonylprop-1-oxyimino)-2-{2-(triphenylmethyl)aminothiazol-4-yl}acetamido]-3-cephem-4-carboxylate dissolved in 10 ml of DMSO was added 350 mg of 1,4-diamino-1,5,6,7-tetrahydro-cyclopentapyrimidine-2-thione synthesized in Preparation Example 1 above and the reaction solution was stirred at room temperature for 3 hours. The reaction solution was extracted with a mixture of 20 ml of tetrahydrofuran and 20 ml of ethyl acetate, and washed with 100 ml of saturated sodium chloride solution. The organic layer was dried over anhydrous magnesium sulfate and distilled under reduced pressure to remove the solvent. The residues so obtained was dissolved in 4 ml of anisole and the resultant solution was cooled to a temperature ranging from 0° to 4° C. Thereto was added 8 ml of trifluoroacetic acid and the resulting solution was stirred at room temperature for 40 minutes and cooled to a temperature ranging from −20° to −30° C., and 50 ml of diethyl ether was added thereto to produce precipitates, which were collected by filtration, washed with 50 ml of acetone and dried to obtain 0.9 g of ivory solids. The solids were purified by a fractional liquid chromatography ($\mu$-Bondapak $C_{18}$ steel column: 19 mm × 30 cm) using as an eluent a 25% methanol solution to obtain 210 mg of the title compound as a white solid.

MS(FAB, M+1): 650

NMR($\delta$, $D_2O$+$NaHCO_3$): 0.94(t, 3H), 1.76(q, 2H), 2.25(m, 2H), 2.76(t, 2H), 3.06(t, 2H), 3.58(ABq, 2H), 4.34 (ABq, 2H) , 4.63 (ABq, 1H) , 5.15 (d, 1H), 5.78(d, 1H), 6.78(s, 1H)

IR(KBr, $cm^{-1}$): 1765 ($\beta$-lactam), 1670, 1610, 1520

Example 24: Synthesis of 7-[(Z)-2-(2-aminothiazol-4-yl }-2-((R)-1-carboxyprop-1-oxyimino)acetamido]-3-(4-amino-1-methyl-1,5,6,7-tetrahydro-cyclopentapyrimidinium-2-yl)thiomethyl-3-cephem-4-carboxylate(I-14(R))

The same procedures as described in Example 23 above were repeated except that 320 mg of 4-amino-1-methyl-1,5,6,7-tetrahydro-cyclopentapyrimidine-2-thione synthesized in preparation Example 2 above was used as a starting material to obtain 210 mg of the title compound as a white powder.

MS(FAB, M+1): 649

NMR($\delta$, $D_2O$+$NaHCO_3$): 0.95(t, 3H), 1.82(q, 2H), 2.23(m, 2H), 2.81(t, 2H), 3.12(t, 2H), 3.56(ABq, 2H), 3.64(s, 3H), 4.36(ABq, 2H), 4.66(q, 1H), 5.15(d, 1H), 5.78(d, 1H), 6.99(s, 1H)

IR(KBr, $cm^{-1}$): 1765($\beta$-lactam), 1660, 1590, 1530

Activity Test

In order to illustrate a surprisingly superior antibacterial effectiveness of the compounds of the present invention, their minimal inhibitory concentrations(MIC) against standard strains were determined and compared with those of Ceftazidime used as a control compound.

These MIC values were taken by employing a two-fold dilution method: that is, two-fold serial dilutions of each of the test compounds were made and dispersed in a Muller-Hinton agar medium; 2 $\mu$l of the standard test strain which had the $10^7$ CFU(Colony Forming Unit) per ml was inoculated on the medium; and these were incubated at 37° C. for 20 hours. The results of the MIC tests are shown in Table 2.

TABLE 2

| | MIC Values against the standard straings($\mu$g/ml) | | | | | | | | |
|---|---|---|---|---|---|---|---|---|---|
| | Compound | | | | | | | | |
| organism/LK Code | I-1 | I-2 | I-5(S) | I-6(S) | I-8 | I-10 | I-11 | I-12 | ceftazidime |
| S. aureus/6538pA | 2 | 2 | 4 | 4 | 2 | 0.25 | 2 | 2 | 16 |
| S. aureus/giorigio | 1 | 1 | 2 | 2 | 2 | 0.13 | 1 | 2 | 4 |
| S. aureus/77 | 4 | 8 | 8 | 4 | 4 | 0.13 | 16 | 8 | 32 |
| E. coli/10536 | 0.063 | 0.13 | 0.016 | 0.016 | 0.016 | 0.016 | 0.016 | 0.016 | 0.063 |
| E. coli/3190Y | 0.016 | 0.063 | <=0.008 | 0.063 | 0.063 | 0.016 | <=0.008 | 0.063 | 0.031 |
| E. coli TEM1/1193E | 0.063 | 0.13 | 0.031 | 0.13 | 0.28 | 0.016 | 0.13 | 0.13 | 0.28 |
| E. coli TEM5/3739E | 0.25 | 0.5 | 2 | 1 | 2 | 0.25 | 0.25 | 0.5 | 8 |
| E. coli TEM9/2639E | 2 | 2 | 8 | 4 | 2 | 0.5 | 2 | 4 | >128 |
| P. aeruginosa/1912E | 0.5 | 0.5 | 1 | 1 | 1 | 2 | 0.5 | 1 | 1 |
| P. aeruginosa/10145 | 1 | 1 | 2 | 2 | 1 | 4 | 1 | 2 | 2 |
| P. aeruginosa/6065Y | 4 | 4 | 8 | 4 | 4 | 16 | 8 | 16 | 32 |
| A. calcoaceticus/15473A | 2 | 1 | 2 | 4 | 4 | 4 | 1 | 2 | 2 |
| E. cloacae/1194E | 4 | 4 | 8 | 4 | 8 | 16 | 4 | 8 | 64 |
| K. aerogenes/1776E | 0.13 | 0.13 | 0.13 | 0.13 | 0.25 | 0.5 | 0.13 | 0.13 | 0.25 |
| S. marcescens/1826E | 0.25 | 0.5 | 0.25 | 0.25 | 0.13 | 0.25 | 0.25 | 0.25 | 0.25 |
| S. typhimunium/14028A | 0.13 | 0.25 | 0.25 | 0.25 | 0.25 | 0.25 | 0.25 | 0.25 | 0.25 |

As can be seen from Table 2, the cephalosporin compounds of the present invention possess potent and broad antibacterial activities against Gram-positive and Gram-negative bacteria as compared with the known cephalosporin antibiotic, ceftazidime.

While the invention has been described in connection with the above specific embodiments, it should be recognized that various modifications and changes as may be apparent to those skilled in the art to which the invention pertains may be made and also fall within the scope of the invention as defined by the claims that follow.

What is claimed is:

1. A cephalosporin compound of formula (I):

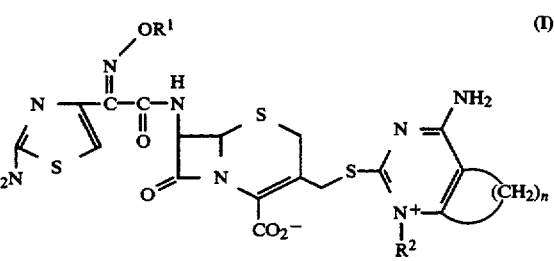

wherein:

$R^1$ is a hydrogen atom or, a $C_{1-4}$ alkyl, $C_{2-4}$ alkenyl, $C_{2-4}$ alkynyl or —$C(R^A)(R^B)COOH$ group wherein $R^A$ and $R^B$ are independently a hydrogen atom or a $C_{1-4}$ alkyl group, or form a $C_{3-7}$ cycloalkyl group together with the carbon atom to which they are attached;

$R^2$ is an amino, $C_{1-4}$ alkyl or $C_{3-7}$ cycloalkyl group; and n is an integer ranging from 2 to 7, and a pharmaceutically acceptable non-toxic salt, physiologically hydrolyzable ester, hydrate and solvate, and isomer thereof.

2. The compound of claim 1 wherein $R^1$ is a methyl or ethyl group, or —$C(R^A)(R^B)COOH$ group where $R^A$ and $R^B$ are independently a hydrogen atom or a methyl or ethyl group, or form a cyclopentyl or cyclohexyl group together with the carbon atom to which they are attached; $R^2$ is a methyl or amino group; and n is 3 or 4.

3. A pharmaceutical composition comprising an effective amount of the cephalosporin compound defined in claim 1 as an active ingredient, and a pharmaceutically acceptable carrier.

* * * * *